US006979560B1

(12) United States Patent
Livshits et al.

(10) Patent No.: US 6,979,560 B1
(45) Date of Patent: Dec. 27, 2005

(54) *ESCHERICHA* BACTERIA OVEREXPRESSING THE YAHN GENE FOR FEEDBACK-INSENSITIVE AMINO ACID PRODUCTION

(75) Inventors: Vitaliy Arkadievich Livshits, Moscow (RU); Natalia Pavlovna Zakataeva, Moscow (RU); Kazuo Nakanishi, Yokohama (JP); Vladimir Veniaminovich Aleshin, Moscow (RU); Petr Vladimirovich Troshin, Moscow (RU); Irina Lyvovna Tokhmakova, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/459,573

(22) Filed: Dec. 13, 1999

(30) Foreign Application Priority Data

Dec. 30, 1998  (RU) ............................................ 98124016
Mar. 9, 1999   (RU) ............................................ 99104431

(51) Int. Cl.⁷ .......................... C12P 13/14; C12P 13/24; C12P 13/08; C12N 1/20; C07K 17/00
(52) U.S. Cl. .................. 435/107; 435/110; 435/252.33; 435/115; 435/320.1; 530/350; 536/23.1
(58) Field of Search ............................ 435/252.33, 107, 435/110, 115, 320.1; 530/350; 536/23.1

(56) References Cited

U.S. PATENT DOCUMENTS

| | | | |
|---|---|---|---|
| 5,175,107 A | 12/1992 | Debabov et al. | |
| 5,538,873 A | 7/1996 | Debabov et al. | |
| 5,631,157 A | 5/1997 | Debabov et al. | |
| 5,658,766 A | 8/1997 | Livshits et al. | |
| 5,705,371 A | 1/1998 | Debabov et al. | |
| 5,976,843 A | 11/1999 | Debabov et al. | |
| 6,040,160 A | * 3/2000 | Kojima et al. | ............... 435/115 |

FOREIGN PATENT DOCUMENTS

EP        0 994 190        4/2000

OTHER PUBLICATIONS

Blattner et al. GenBank Accession No. P75693 Nov. 1, 1997.*
Vrljic et al. Mol Microbiol (1996) 22(5):815–826.*
Aleshin et al., Trends Biochem Sci, Apr. 1999, 24(4):133–135.
F.R. Blattner, et al., Journal=Science 277, pp. 1–8, Acc. AE000344, Definition=*Escherichia coli* K–12 MG1655 section 234 of 400 of the complete genome, "The Complete Genome Sequence of *Escherichia coli* K–12," Jan. 16, 1997.
F.R. Blattner, et al., Journal=Science 277, pp. 1–7, Acc. AE000375, Definition=*Escherichia coli* K–12 MG1655 section 265 of 400 of the complete genome, "The Complete Genome Sequence of *Escherichia coli* K–12," Jan. 16, 1997.
F.R. Blattner, et al., Journal=Science 277, pp. 1–9, Acc. AE000140, Definition=*Escherichia coli* K–12 MG1655 section 30 of 400 of the complete genome, "The Complete Genome Sequence of *Escherichia coli* K–12," Jan. 16, 1997.
F.R. Blattner, et al., Journal=Science 277, pp. 1–10, Acc. AE000274, Definition=*Escherichia coli* K–12 MG1655 section 164 of 400 of the complete genome, "The Complete Genome Sequence of *Escherichia coli* K–12," Jan. 16, 1997.
N.P. Zakataeva, et al., Faseb Journal, vol. 11, No. 9, p. A935, "Characterization of a Pleiotropic Mutation that Confers Upon *Escherichia coli* Cells Resistance to High Concentrations of Homoserine and Theronini", 1997.
M. Duncan, et al., Database EMBL/Swissprot (Online) ID: Yahn–Ecoli, "The Complete Genome Sequence of *Escherichia coli* K–12.", Nov. 1, 1997.
T. Itoh, et al., Database EMBL/Swissprot (Online) ID: YEAS_ECOLI, "A 460–kb DNA Sequence of the *Escherichia coli* K–12 Genome Corresponding to the 40.1–50.0 MIN Region on the Linkage Map," Jul. 15, 1998.
H. Aiba, et al., Database EMBL/Swissprot (Online) ID: YFIK_ECOLI, "Non–Ribosomal Proteins Affecting the Assembly of Ribosomes in *Escherichia coli*," Oct. 1, 1994.
P.R. Alefounder, et al., Database EMBL/Swissprot (Online) ID: YGGA_ECOLI, "Identification, Molecular Cloning and Sequence Analysis of a Gene Cluster Encoding the Class II Fructose 1,6–Bisphosphate Aldolase, 3–Phosphoglycerate Kinase and a Putative Second Glyceraldehyde 3–Phosphate Dehydrogenase of *Escherichia coli*," Oct. 1, 1989.

* cited by examiner

Primary Examiner—Rebecca E. Prouty
Assistant Examiner—Delia M. Ramirez
(74) Attorney, Agent, or Firm—Shelly Guest Cermak

(57) ABSTRACT

A bacterium belonging to the genus *Escherichia* and having an ability to produce an L-amino acid, wherein the ability to produce the L-amino acid is increased by increasing an expression amount of an L-amino acid excretion protein, and a method for producing the L-amino acid using the bacterium.

6 Claims, No Drawings

ESCHERICHA BACTERIA OVEREXPRESSING THE YAHN GENE FOR FEEDBACK-INSENSITIVE AMINO ACID PRODUCTION

TECHNICAL FIELD

The present invention relates to a method for producing an amino acid. In particular, the present invention relates to an L-amino acid-producing bacterium belonging to the genus *Escherichia* and a method for producing L-amino acids, more specifically, L-glutamic acid, L-lysine, L-threonine, L-alanine, L-histidine, L-proline, L-arginine, L-valine, and L-isoleucine, using the bacterium.

BACKGROUND ART

For production of an L-amino acid by fermentation, a strain isolated from the natural world or an artificial mutant of the strain has been used to improve productivity. For example, in the case of L-lysine, many artificial mutants producing L-lysine are known, and most of them are mutants resistant to S-2-aminoethylcysteine (AEC) and belong to the genus *Brevibacterium, Corynebacterium, Bacillus* or *Escherichia*. Also, there have been proposed various technics for increasing amino acid production such as use of a transformant obtained by using a recombinant DNA (U.S. Pat. No. 4,278,765).

The technics are mostly based on enhancement of an activity of an enzyme involved in an amino acid biosynthetic pathway, conversion of the enzyme to that desensitized in inhibition and the like (As to bacterium belonging the genus *Escherichia*, see Japanese Patent Application Laid-Open No. 56–18596 (1981) and International Publication No. WO 95/16042).

On the other hand, as an example of improvement of amino acid productivity by enhancing an amino acid excretion protein, a bacterium belonging to the genus *Corynebacterium* in which an L-lysine excretion gene, lysE is enhanced is known. However, as to bacteria belonging to the genus *Escherichia*, it is unknown even whether an L-amino acid excretion protein is present or not. Therefore, it is unknown whether enhancement of the L-amino acid excretion protein is effective in L-amino acid production using a bacterium belonging to the genus *Escherichia* or not.

Although the entire nucleotide sequence of *E. coli* strain K-12 belonging to the genus *Escherichia* has been already determined (Science, 277, 1453–1474(1997)), there are a large number of proteins of which functions are unknown.

DISCLOSURE OF THE INVENTION

An object of the present invention is to obtain a protein participating in excretion of an L-amino acid, thereby providing a strain improved in L-amino acid productivity and an improved method for producing an L-amino acid by fermentation.

The inventors have conducted screening for the protein participating in excretion of an L-amino acid. As a result, the present inventors have found that a yield of an L-amino acid based on consumed sugar is increased when a particular gene is enhanced. On the basis of the finding, the present invention has been completed.

Thus, the present invention provides a bacterium belonging to the genus *Escherichia* and having an ability to produce an L-amino acid, wherein the ability to produce the L-amino acid is increased by increasing an expression amount of at least one protein selected from the group consisting of the following proteins of (A) to (H) (hereinafter also referred to as "the bacterium of the present invention"):

(A) a protein having an amino acid sequence shown in SEQ ID NO: 10 in Sequence Listing;

(B) a protein which has an amino acid sequence including deletion, substitution, insertion, addition or inversion of one or several amino acids in the amino acid sequence shown in SEQ ID NO: 10 in Sequence Listing, and which has an activity of increasing the ability to produce the L-amino acid of the bacterium having the protein;

(C) a protein having an amino acid sequence shown in SEQ ID NO: 12 in Sequence Listing;

(D) a protein which has an amino acid sequence including deletion, substitution, insertion, addition or inversion of one or several amino acids in the amino acid sequence shown in SEQ ID NO: 12 in Sequence Listing, and which has an activity of increasing the ability to produce the L-amino acid of the bacterium having the protein;

(E) a protein having an amino acid sequence shown in SEQ ID NO: 14 in Sequence Listing;

(F) a protein which has an amino acid sequence including deletion, substitution, insertion, addition or inversion of one or several amino acids in the amino acid sequence shown in SEQ ID NO: 14 in Sequence Listing, and which has an activity of increasing the ability to produce the L-amino acid of the bacterium having the protein;

(G) a protein having an amino acid sequence shown in SEQ ID NO: 16 in Sequence Listing; or (H) a protein which has an amino acid sequence including deletion, substitution, insertion, addition or inversion of one or several amino acids in the amino acid sequence shown in SEQ ID NO: 16 in Sequence Listing, and which has an activity of increasing the ability to produce the L-amino acid of the bacterium having the protein.

The bacterium of the present invention preferably an L-lysine-producing bacterium in which an expression amount of at least one protein selected from the group consisting of the proteins (A) to (D), (G) and (H) is increased; an L-glutamic acid-producing bacterium in which an expression amount of at least one protein selected from the group consisting of the proteins (A) to (H) is increased; an L-alanine-producing bacterium in which an expression amount of at least one protein selected from the group consisting of the proteins (C) and (D) is increased; an L-valine-producing bacterium in which an expression amount of at least one protein selected from the group consisting of the proteins (C) and (D) is increased; an L-histidine-producing bacterium in which an expression amount of at least one protein selected from the group consisting of said proteins (C) to (F) is increased; an L-proline-producing bacterium in which an expression amount of at least one protein selected from the group consisting of said proteins (A) to (F) is increased; an L-threonine-producing bacterium in which an expression amount of at least one protein selected from the group consisting of said proteins (E) and (F) is increased; an L-arginine-producing bacterium in which an expression amount of at least one protein selected from the group consisting of said proteins (G) and (H) is increased; or an L-isoleucine-producing bacterium in which an expression amount of at least one protein selected from the group consisting of said proteins (C) and (D) is increased.

Preferably, in the bacterium of the present invention, a copy number of a DNA coding for said protein in a cell is increased. The DNA is preferably carried on a multicopy vector in the cell or on a transposon in the cell.

The present invention also provides a method for producing an L-amino acid, comprising the steps of:
cultivating the bacterium of the present invention in a culture medium, to produce and accumulate the L-amino acid in the medium, and
recovering the L-amino acid from the medium (hereinafter also referred to as "the method of the present invention").

The method of the present invention preferably an L-lysine production method using an L-lysine-producing bacterium in which an expression amount of at least one protein selected from the group consisting of the proteins (A) to (D), (G) and (H) is increased; an L-glutamic acid production method using an L-glutamic acid-producing bacterium in which an expression amount of at least one protein selected from the group consisting of the proteins (A) to (H) is increased; an L-alanine production method using an L-alanine-producing bacterium in which an expression amount of at least one protein selected from the group consisting of the proteins (C) and (D) is increased; an L-valine production method using an L-valine-producing bacterium in which an expression amount of at least one protein selected from the group consisting of the proteins (C) and (D) is increased; an L-histidine production method using an L-histidine-producing bacterium in which an expression amount of at least one protein selected from the group consisting of said proteins (C) to (F) is increased; an L-proline production method using an L-proline-producing bacterium in which an expression amount of at least one protein selected from the group consisting of said proteins (A) to (F) is increased; an L-threonine production method using an L-threonine-producing bacterium in which an expression amount of at least one protein selected from the group consisting of said proteins (E) and (F) is increased; an L-arginine production method using an L-arginine-producing bacterium in which an expression amount of at least one protein selected from the group consisting of said proteins (G) and (H) is increased; or an L-isoleucine production method using an L-isoleucine-producing bacterium in which an expression amount of at least one protein selected from the group consisting of said proteins (C) and (D) is increased.

Preferably, in the method of the present invention, a copy number of a DNA coding for said protein in a cell of the bacterium is increased. The DNA is preferably carried on a multicopy vector in the cell, or on a transposon in the cell.

According to the present invention, an ability to produce an L-amino acid of a bacterium belonging to the genus *Escherichia* can be increased. Also, a method for producing an L-amino acid can be improved in a production rate of an L-amino acid.

The present invention will be explained in detail below. Hereinafter, an amino acid is of L-configuration unless otherwise noted.

<1> Bacterium of the Present Invention

The bacterium of the present invention is a bacterium belonging to the genus *Escherichia* and having an ability to produce an amino acid, in which the ability to produce the amino acid is increased by increasing an expression amount of a protein which has an activity of increasing the ability to produce the amino acid of the bacterium, or an activity of increasing resistance to an amino acid or amino acid analogue. Hereinafter, the protein is referred to as "amino acid excretion protein" for the sake of convenience. However, the term does not mean that function of the protein is limited to amino acid excretion.

Examples of the amino acid excretion protein include a protein having an amino acid sequence shown in SEQ ID NO: 10, a protein having an amino acid sequence shown in SEQ ID NO: 12, a protein having an amino acid sequence shown in SEQ ID NO: 14 and a protein having an amino acid sequence shown in SEQ ID NO: 16.

The amino acid excretion protein may have selectivity to amino acid. An amino acid excretion protein appropriate for each amino acid can be determined by allowing the amino acid excretion protein to be expressed in a bacterium belonging to the genus *Escherichia* and having an ability to produce the amino acid, and measuring an increase of a yield of the amino acid or measuring an increase of a minimum inhibition concentration (MIC) of an amino acid or amino acid analogue.

For example, in the case of lysine, a protein having an amino acid sequence shown in SEQ ID NO: 10, 12 or 16 is effective; in the case of glutamic acid, a protein having an amino acid sequence shown in SEQ ID NO: 10, 12, 14 or 16 is effective; in the case of alanine, a protein having an amino acid sequence shown in SEQ ID NO: 12 is effective; in the case of valine, a protein having an amino acid sequence shown in SEQ ID NO: 12 is effective; in the case of histidine, a protein having an amino acid sequence shown in SEQ ID NO: 12 or 14; in the case of proline, a protein having an amino acid sequence shown in SEQ ID NO: 10, 12 or 14 is effective; in the case of threonine, a protein having an amino acid sequence shown in SEQ ID NO: 14 is effective; in the case of arginine, a protein having an amino acid sequence shown in SEQ ID NO: 16 is effective; and in the case of isoleucine, a protein having an amino acid sequence shown in SEQ ID NO: 12 is effective.

The term "an expression amount is increased" used herein usually means that the expression amount is larger than that in a wild strain of *E. coli* such as strain MG1655 or W3110. The terms also means that when a strain is obtained by modification through genetic engineering technics or the like, the expression amount is larger than that prior to the modification. The expression amount of the amino acid excretion protein may be determined directly by the determination of the amino acid excretion protein or indirectly by the determination of MIC of an amino acid or amino acid analogue or of amino acid productivity of a bacterium belonging to the genus *Escherichia* and having the amino acid excretion protein.

The method for increasing the expression amount of the amino acid excretion protein is exemplified by a method for increasing a copy number of DNA encoding the amino acid excretion protein in a cell of the bacterium.

For increasing the copy number in the cell, a DNA fragment coding for the amino acid excretion protein may be ligated to a vector which functions in a bacterium belonging to the genus *Escherichia* to produce a recombinant DNA, which is introduced to a host to transform it. The copy number of the gene coding for the amino acid excretion protein (amino acid excretion protein gene) in the cell of the transformant strain increases, thereby increasing the expression amount of the amino acid excretion protein. The vector is preferably a multicopy vector.

The increase of the copy number in the cell can be achieved by allowing plural copies of the amino acid excretion protein gene to exist on chromosomal DNA of the host. The introduction of plural copies of the amino acid excretion protein gene to chromosomal DNA of a bacterium belonging to the genus *Escherichia*, may be conducted through homologous recombination by using a sequence of which plural copies exist on the chromosomal DNA, as a target. As the sequence of which plural copies exist on the chromosomal DNA, a repetitive DNA and an inverted repeat present in a terminal portion of a transposable element may be used.

Alternatively, as disclosed in Japanese Patent Application Laid-Open No. 2-109985 (1990), the plural copies can be introduced to the chromosomal DNA by making the amino acid excretion protein gene carried on a transposon and allowing the transposon to be transposed, which is preferred. According to any of the above-mentioned methods, the copy number of the amino acid excretion protein gene in the transformant strain increases, thereby increasing the expression amount of the amino acid excretion protein.

The multicopy vector is exemplified by plasmid vectors such as pBR322, pMW118, pUC19 or the like, and phage vectors such as λ1059, λBF101, M13mp9 or the like. The transposon is exemplified by Mu, Tn10, Tn5 or the like.

The introduction of a DNA into a bacterium belonging to the genus *Escherichia* can be performed, for example, by a method of D. M. Morrison (Methods in Enzymology 68, 326 (1979)) or a method in which recipient bacterial cells are treated with calcium chloride to increase permeability of DNA (Mandel, M. and Higa, A., J. Mol. Biol., 53, 159 (1970)) and the like.

Besides the above-mentioned gene amplification, the increase of the expression amount of the amino acid excretion protein can be also achieved by replacing an expression regulatory sequence such as a promoter of the amino acid excretion protein gene with stronger one (see Japanese Patent Application Laid-Open No. 1-215280 (1989)). For example, lac promoter, trp promoter, tac promoter, $P_R$ promoter and $P_L$ promoter of lambda phage, and the like are known as a strong promoter. The replacement with the promoter enhances expression of the amino acid excretion protein, thereby increasing the expression amount of the amino acid excretion protein. The enhancement of the expression regulatory sequence may be combined with the increase of the copy number of the amino acid excretion protein.

In the bacterium of the present invention, expression amounts of plural amino acid excretion proteins may be increased.

The amino acid excretion protein is encoded by genes which are known as yahN gene, yeaS gene, yfiK gene and yggA gene and of which functions are unknown. Therefore, the DNA encoding the amino acid excretion protein can be obtained by synthesizing primers based on the known sequences (for example, the entire nucleotide sequence of chromosome of *Escherichia coli* strain K-12 has been already determined (Science, 277, 1453–1474(1997))), and conducting amplification by PCR using chromosomal DNA of a bacterium belonging to the genus *Escherichia* as a template. Also, the object DNA fragment can be selected by hybridization from a chromosomal DNA library of a bacterium belonging to the genus *Escherichia* by preparing a probe based on the known sequences. Alternatively, the DNA encoding the amino acid excretion protein may be synthesized based on the known sequences. The nucleotide sequence of the DNA encoding the amino acid excretion protein is exemplified by that shown in SEQ ID NO: 9, 11, 13 or 15 in the Sequence Listing.

Methods for preparation of chromosomal DNA, preparation of chromosomal DNA library, hybridization, PCR, preparation of plasmid DNA, digestion and ligation of DNA, transformation, selection of an oligonucleotide as a primer and the like may be ordinary methods well known to one skilled in the art. These methods are described in Sambrook, J., Fritsch, E. F., and Maniatis, T., "Molecular Cloning A Laboratory Manual, Second Edition", Cold Spring Harbor Laboratory Press (1989) and the like.

The amino acid excretion protein may comprise substitution, deletion, insertion, addition or inversion of one or several amino acids at one or a plurality of positions, provided that the activity of increasing the ability to produce the amino acid of the bacterium belonging to the genus *Escherichia* and having the protein is not deteriorated. The term "several" may vary depending on a position in a steric structure of the protein and a kind of an amino acid residue. It is because some amino acids such as isoleucine and valine have high similarity to each other, and a difference between such the amino acids does not largely affect the steric structure of the protein.

The DNA which codes for the substantially same protein as the amino acid excretion protein as described above, may be obtained, for example, by modifying the nucleotide sequence, for example, by means of the site-directed mutagenesis method so that one or more amino acid residues at a specified site involve substitution, deletion, insertion, addition or inversion. The DNA modified as described above may be obtained by the conventionally known mutation treatment. The mutation treatment includes a method for treating a DNA coding for the amino acid excretion protein in vitro, for example, with hydroxylamine, and a method for treating a microorganism, for example, a bacterium belonging to the genus *Escherichia*, harboring a DNA coding for the amino acid excretion protein with ultraviolet irradiation or a mutating agent such as N-methyl-N'-nitro-N-nitrosoguanidine (NG) and nitrous acid usually used for the mutation treatment.

The substitution, deletion, insertion, addition or inversion of the one or more amino acid residues includes a naturally-occurring mutation or variation which is resulted from a difference between individual microorganisms having the amino acid excretion protein and a difference between species, strains or the like.

The DNA, which codes for substantially the same protein as the amino acid excretion protein, can be obtained by allowing a DNA having the mutation as described above to be expressed in a cell of an appropriate bacterium belonging to the genus *Escherichia*, and investigating the increase of amino acid productivity of the cell.

Also, the DNA, which codes for substantially the same protein as the amino acid excretion protein, can be obtained by isolating a DNA which hybridizes with DNA having, for example, a nucleotide sequence shown in SEQ ID NO: 9, 11, 13 or 15 in sequence Listing under stringent conditions, and which codes for a protein having the activity of increasing the ability to produce the amino acid of the bacterium belonging to the genus *Escherichia*, from DNAs encoding the amino acid excretion proteins having mutations or cells containing the DNAs. The term "stringent conditions" referred to herein means a condition under which a specific hybrid is formed, and a non-specific hybrid is not formed. It is difficult to clearly express this condition by using any numerical value. However, for example, the stringent conditions include a condition under which DNAs having high homology, for example, DNAS having homology of not less than 70% with each other are hybridized, and DNAs having homology lower than the above with each other are not hybridized, or a condition of a salt concentration corresponding to 60° C., 1×SSC, 0.1% SDS, preferably 0.1×SSC, 0.1% SDS which is a washing condition of ordinary Southern hybridization.

Although there may be a gene in which a stop codon is made in the middle, or a gene encoding a protein losing the activity due to mutation of the active center among the genes which hybridize under such the condition, such genes can be easily eliminated by ligating the genes to a commercially available activity-expression vector and determining the activity of increasing the ability to produce the amino acid of the bacterium belonging to the genus *Escherichia* as described above.

The term "DNA coding for a protein" used herein means a DNA of which one of strands codes for the protein when the DNA is double-stranded.

By increasing an expression amount of an amino acid excretion protein in an amino acid-producing bacterium belonging to the genus *Escherichia* as described above, a produced amount of the amino acid can be increased. As the bacterium belonging to the genus *Escherichia* in which the expression amount of the amino acid excretion protein is to be increased, strains which have abilities to produce desired amino acids (amino acid productivities) are used. Besides, an ability to produce an amino acid may be imparted to a bacterium in which the expression amount of the amino acid excretion protein is increased. Examples of amino acid-producing bacteria belonging to the genus *Escherichia* include *E. coli* AJ13199 (FR patent No. 2747689), and those obtainable from known materials (e.g., *E. coli* W3110 (tyrA)/pCABD2, *E. coli* VL614, *E. coli* VL2054, *E. coli* VL2160, *E. coli* VL2151, *E. coli* W3350 argE::Tn10/pKA10 as described in the Examples below).

For reference, the amino acid excretion protein according to the present invention was identified for the first time as described below.

The present inventors have identified rhtB and rhtC as threonine excretion protein genes of a bacterium belonging to the genus *Escherichia*. The present inventors searched databases based on a hypothesis that amino acid excretion proteins may share a common structure. Namely, BLAST and PSI-BLAST search (Altschul, S. F. et al., Nucleic Acids Res., 25, 3389–3402(1997)) for homology of a protein encoded by rhtB was performed in GenBank CDS, PDB, SWISS-PROT, Spupdate and PIR. Tblastn search was performed in unfinished microbial genomes. BLITZ search (Sturrock, S. S., and Collins, J. F., Mpsch version 1.3. Biocomputing research unit University of Edinburgh, UK (1993)) was performed in SWALL database. SMART search (Ogiwara, I. et al., Protein Sci., 5, 1991–1999 (1996)) was performed in the databases of translations and SWISS-PROT. From the samples of more than 60 sequences found, YeaS (corresponding to f212 of ACCESSION No. AE000274 in GenBank), YahN (corresponding to f223 of ACCESSION No. AE000140 in GenBank), YfiK (corresponding to o195 of ACCESSION No. AE000344 in GenBank) and YggA (corresponding to f211 of ACCESSION No. AE000375 in GenBank) remained as proteins which may have similar function to RhtB, among those originating from *E. coli*. Since functions of any of these genes were unknown, the genes were actually obtained, and effects thereof on MIC of amino acids and amino acid analogues and on amino acid production were examined by enhancing activities thereof. As a result, an effect of increasing MIC of some amino acids and analogues was found with respect to YeaS, YfiK, YahN and YggA. Further examination has revealed that proteins encoded by these genes exhibit an effect of increasing an amino acid accumulation, although they may have some amino acid selectivities.

<2> Method of the Present Invention

The method of the present invention comprises the steps of cultivating the bacterium of the present invention, in a culture medium, to produce and accumulate the amino acid in the medium, and recovering the amino acid from the medium.

Suitable amino acids include lysine, glutamic acid, alanine, valine, histidine, proline, threonine, arginine, and isoleucine.

In the method of present invention, the cultivation of the bacterium belonging to the genus *Escherichia*, the collection and purification of amino acid from the liquid medium may be performed in a manner similar to those of the conventional method for producing an amino acid by fermentation using a bacterium. A medium used in cultivation may be either a synthetic medium or a natural medium, so long as the medium includes a carbon and a nitrogen source and minerals and, if necessary, nutrients which the bacterium used requires for growth in appropriate amounts. The carbon source may include various carbohydrates such as glucose and sucrose, and various organic acids. Depending on assimilatory ability of the used bacterium, alcohol including ethanol and glycerol may be used. As the nitrogen source, ammonia, various ammonium salts such as ammonium sulfate, other nitrogen compounds such as amines, a natural nitrogen source such as peptone, soybean hydrolyte and digested fermentative microbe are used. As minerals, mono-potassium phosphate, magnesium sulfate, sodium chloride, ferrous sulfate, manganese sulfate, calcium carbonate are used.

The cultivation is preferably culture under an aerobic condition such as a shaking culture, and an aeration and stirring culture. The temperature of culture is usually 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the target amino acid in the medium.

Recovering the amino acid can be performed by removing solids such as cells from the medium by centrifugation or membrane filtration after cultivation, and then collecting and purifying the target amino acid by ion exchange, concentration and crystalline fraction methods and the like.

BEST MODE FOR CARRYING OUT THE INVENTION

The present invention will be more concretely explained below with reference to Examples.

EXAMPLE 1

Preparation of the DNA Fragments Which Code for Amino Acid Excretion Proteins

The entire nucleotide sequence of chromosome of *E. coli* strain K-12 has been determined (Science, 277, 1453–1474, 1997). Based on the reported nucleotide sequence, primers were synthesized and the genes yahN, yfiK, yeaS and yggA were amplified by PCR.

(1). Chromosomal DNA of the *E. coli* Strain MG1655 was Used as a Template.

The chromosomal DNA was preapared by an ordinary method (Sambrook, J., Fritsch E. F. and Maniatis T. (1989) Molecular cloning: a laboratory manual, 2 nd ed. Cold Spring Harbor Laboratory Press, Cold Spring Harbor, N.Y.). In the PCR reaction, a standard condition described in "PCR protocols. Current methods and applications". (White, B. A., ed. Humana Press, Totowa, N.J., 1993) was used. The obtained PCR products were purified by an ordinary method and digested with restriction enzymes as described below.

The yahN gene was amplified by using the primers No. 1 and No. 2.

Primer No. 1: gtgtggaaccgacgccggat (a sequence complementary to a sequence of from 1885 base to 1904 base in a nucleotide sequence registered under ACCESSION No. AE000140 in GenBank; SEQ ID NO: 17), and Primer No. 2: tgttgtatggtacggggttcgag (a sequence of from 223 base to 245 base in the same; SEQ ID NO: 18).

The obtained PCR product after purification was digested with restriction enzymes PstI and StuI and ligated to vector pUC21 (Vieira, Messing, Gene, 100, 189–194, 1991) digested with the enzymes PstI and EcoRV by using a ligation kit. Then, transformation of competent cells of E. coli TG1 (Sambrook, J., Fritsch E. F. and Maniatis T. (1989) Molecular cloning: a laboratory manual, 2nd ed. Cold Spring Harbor Laboratory Press, Cold Spring Harbor, N.Y.) with the product was conducted and the cells were spread on L medium (10 g/l Bacto trypton, 5 g/l Yeast extract, 5 g/l NaCl, 15 g/l agar, pH 7.0) containing 10/m/ml IPTG (isopropyl-β-D-thiogalactopyranoside) and 40/m/ml X-gal (5-bromo-4-chloro-3-indolyl-β-D-galactoside) and 100/m/ml ampicillin, and cultured overnight. Appeared white colonies were picked up and subjected to single colony isolation to obtain transformants. Plasmid was prepared from the transformants using an alkali extraction method and designated as pYAHN.

The yeaS gene was amplified by using the primers No. 3 and No. 4.

Primer No. 3: ctttgccaatcccgtctccc (a sequence complementary to a sequence of from 7683 base to 7702 base in a nucleotide sequence registered under ACCESSION No AE000274 in GenBank; SEQ ID NO: 19);

Primer No. 4: gccccatgcataacggaaag (a sequence of from 5542 base to 5561 base in the same; SEQ ID NO: 20).

The obtained PCR product after purification was digested with a restriction enzyme AvaI and ligated to vector pUC19. After transformation of E. coli TG1 as above, the plasmid designated as pYEAS was obtained.

The yfiK gene was amplified by using the primers No. 5 and No. 6.

Primer No. 5: gaagatcttgtaggccggataaggcg (a sequence of from 4155 base to 4177 base in a nucleotide sequence registered under ACCESSION No AE000344 in GenBank, with a restriction enzyme BglIIo site added at the 5'-end thereof; SEQ ID NO: 21)

Primer No. 6: tggttttaccaattggccgc (a sequence complementary to a sequence of from 6307 base to 6326 base in the same; SEQ ID NO: 22).

The obtained PCR product after purification was digested with restriction enzymes BglII and MunI and ligated to vector pUC21 digested with restriction enzymes BglII and EcoRI. After transformation of E. coli TG1 as above, the plasmid designated PYFIK was obtained.

The yggA gene was amplified by using the primers No. 7 and No. 8.

Primer No. 7: acttctcccgcgagccagttc (a sequence complementary to a sequence of from 9606 base to 9626 base in a nucleotide sequence registered under ACCESSION No AE000375 in GenBank; SEQ ID NO: 23).

Primer No. 8: ggcaagcttagcgcctctgtt (a sequence of from 8478 base to 8498 base in the same; SEQ ID NO: 24).

The obtained PCR product after purification was digested with restriction enzymes HindIII and ClaI and ligated to vector pOK12 (Vieira, Messing, Gene, 100, 189–194, 1991) digested with the same restriction enzymes. After transformation of E. coli TG1 as above, the plasmid designated pYGGA was obtained.

(2). Chromosomal DNA of the E. coli Strain W3110 was Used as a Template.

The yahN gene was amplified by using the primers No. 9 (SEQ ID NO 1) and No. 10 (SEQ ID NO. 2).

The yeaS gene was amplified by using the primers No. 11 (SEQ ID NO 3) and No. 12 (SEQ ID NO 4).

The yfiK gene was amplified by using the primers No. 13 (SEQ ID NO 5) and No. 14 (SEQ ID NO 6).

The yggA gene was amplified by using the primers No. 15 (SEQ ID NO 7) and No. 16 (SEQ ID NO 8).

The obtained PCR product was purified, digested with restriction enzymes SacI and XbaI (EcoRI and PstI for yggA), and ligated to plasmid pMW118 (Nippon Gene). The plasmid into which a DNA fragment of which sequence was identical to the reported sequence was inserted was designated as follows:

one carrying yahN: pMW118::yahN
One carrying yeaS: pMW118::yeaS
One carrying yfiK: pMW118::yfiK
One carrying yggA: pMW118::yggA

EXAMPLE 2

Effect of the yahN, yeaS, yfiK, and yggA DNA Fragments Amplification on the E. coli TG1 Resistance to Some Amino Acids and Amino Acid Analogues The homology of the yeaS, yfiK, yahN and yggA gene products with the lysine transporter, LysE, of Corynebacterium glutamicum (Vrljic et al., Mol. Microbiol.,22, 815–826, 1996) and RhtB protein involved in homoserine excretion, indicates the analogues function for these proteins. It is well known that the increased expression of the genes involved in antibiotic and heavy metal efflux increases the level of resistance to the drugs (Nikaido, H. J. Bacteriology, 178, 5853–5859, 1996). Therefore, the effect of the pYEAS, pYAHN, PYFIK, and pYGGA plasmids on susceptibility of the strain TG1 to some amino acids and amino acid analogues was tested. Overnight cultures of the E. coli strains TG1/pYEAS, TG1/pYAHN, TG1/pYFIK, TG1/pYGGA and of the control strains TG1/pUC21, TG1/pUC19 and TG1/pOK12 grown in M9 minimal medium with an appropriate antibiotic on a rotary shaker ($10^9$ cfu/ml) were diluted 1:100 in M9 minimal medium and grown for 5 h in the same medium. Then the log phase cultures thus obtained were diluted and about $10^4$ alive cells were applied to well-dried test plates with M9 agar containing doubling increments of amino acids or analogues. Thus the minimum inhibition concentration (MIC) of these compounds were examined.

The results are shown in Table 1. It follows from the Table 1 that multiple copies of yfiK gene conferred increased resistance to proline, homoserine, histidine, threonine, glutamate, lysine, α-amino-β-hydroxyvaleric-acid (AHVA), S-(2-aminoethyl)-L-cysteine (AEC) and α-aminobutyric acid; multiple copies of yahN gene conferred increased resistance to proline, multiple copies of yeaS gene conferred increased resistance to threonine, homoserine, lysine, glutamate, histidine, proline and α-aminobutyric acid; multiple copies of yggA gene conferred increased resistance to S-(2-aminoethyl)-L-cysteine (AEC), lysine, and arginine. These results indicate that except for YahN, every of the presumed transporters have specificity to several substrates (amino acids and amino acid analogues), or may show non-specific effects as a result of amplification.

TABLE 1

| Substrate | MIC (μg/ml) for *E. coli* TG1, harboring the plasmid | | | | |
|---|---|---|---|---|---|
| | pUC21 | pYFIK | pYAHN | pYEAS | pYGGA |
| L-homoserine | 500 | 1000 | 500 | 1000 | 500 |
| L-threonine | 30000 | 40000 | 30000 | 50000 | 30000 |
| L-lysine | 5000 | 7500 | 5000 | 7500 | 15000 |
| L-glutamate (Na salt) | 5000 | 10000 | 5000 | 20000 | 5000 |
| L-histidine | 5000 | 10000 | 5000 | 30000 | 5000 |
| L-valine | 0.5 | 0.5 | 0.5 | 0.5 | 0.5 |
| L-proline | 1000 | 5000 | 2000 | 2000 | 1000 |
| L-arginine | 10000 | 10000 | 10000 | 10000 | 20000 |
| AHVA | 100 | 200 | 100 | 100 | 100 |
| AEC | 5 | 10 | 5 | 5 | 200 |
| α-aminobutyric acid | 2500 | 5000 | 2500 | >10000 | 2500 |
| 4-aza-DL-leucine | 100 | 100 | 100 | 100 | 100 |

EXAMPLE 3

Effect of yeaS, yahN, and yfiK DNA Fragments Amplification on Glutamic Acid Production The *E. coli* strain AJ13199 (FR patent No. 2747689) was transformed with the vector pUC21 and each of the plasmids pYAHN, pYEAS and pYFIK. Thus the strains AJ13199/pUC21 (VKPM B-7728), AJ13199/pYAHN (VKPM B-7729), AJ13199/pYEAS (VKPM B-7731), and AJ13199/pYFIK (VKPM B-7730) were obtained.

These strains were each cultivated at 37° C. for 18 hours in a nutrient broth with 100 mg/l ampicillin, and 0.3 ml of the obtained culture was inoculated into 3 ml of a fermentation medium containing 100 mg/l ampicillin, in a 20×200 mm test tube, and cultivated at 37° C. for 48 hours with a rotary shaker. After the cultivation, an accumulated amount of glutamic acid in the medium was determined by known method.

| The composition of the fermentation medium (g/l): | |
|---|---|
| Glucose | 80 |
| $(NH_4)_2SO_4$ | 22 |
| $K_2HPO_4$ | 2 |
| NaCl | 0.8 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 (dry-heat-sterilized at 180° C. for 2 h) |

(Glucose and $K_2HPO_4$ separately sterilized)

The results are shown in Table 2. As shown in Table 2, the strains AJ13199/pYAHN, AJ13199/pYEAS, and AJ13199/pYFIK accumulated glutamic acid in a larger amount than the strain AJ13199/pUC21 in which an expression amount of amino acid excretion proteins was not enhanced.

TABLE 2

| Strain | Glutamic acid, g/l |
|---|---|
| AJ13199/pUC21 | 21.9 |
| AJ13199/pYAKN | 27.9 |
| AJ13199/pYEAS | 29.7 |
| AJ13199/pYFIK | 28.4 |

EXAMPLE 4

Effect of yeaS, yahN, and yfiK DNA Fragments Amplification on Lysine Production (1). As the lysine-producing bacterium belonging to the genus *Escherichia*, *E. coli* strain W3110 (TyrA) described in European Patent Publication No. 488424 to which plasmid pCABD2 was introduced, described in International (Publication No. WO 95/16042, was used. Specifically, plasmid pCABD2, and each of the plasmid pMW118::yahN, pMW118::yeaS, pMW118::yfiK and pMW118 were introduced to *E. coli* strain W3110 (TyrA) to obtain the following strains:

W3110 (tyrA)/pCABD2+pMW118::yahN
W3110 (tyrA)/pCABD2+pMW118::yeaS
W3110 (tyrA)/pCABD2+pMW118::yfik
W3110 (tyrA)/pCABD2+pMW118.

Lysine productivity of these strains was estimated by culture. The composition of the used medium was as follows (g/l):

| | |
|---|---|
| Glucose | 40.0 |
| $MgSO_4 \cdot 7H_2O$ | 1.0 |
| $(NH_4)_2SO_4$ | 16.0 |
| $K_2HPO_4$ | 1.0 |
| $FeSO_4 \cdot 7H_2O$ | 0.01 |
| $MnSO_4 \cdot 7H_2O$ | 0.01 |
| Yeast extract (Difco) | 2.0 |
| Tyrosine | 0.1 |

Adjusted to pH 7.0 and autoclaved at 115° C. for 10 minutes. (Glucose and $MgSO_4 7H_2O$ separately sterilized). Pharmacopeial $CaCO_3$ 25 g/l (dry-heat-sterilized at 180° C. for 2 h).

As antibiotics, 20 mg/l of streptomycin and 50 mg/l of ampicillin were added depending on a kind of a plasmid. Cultivation was conducted at 37° C. for 30 hours with agitation at 115 rpm. The results are shown in Table 3.

TABLE 3

| Strain | Lysine, g/l | Yield, (%) |
|---|---|---|
| W3110(tyrA) | 0.08 | 0.2 |
| W3110(tyrA)/pCABD2 + pMW118 | 12.2 | 30.5 |
| W3110(tyrA)/pCABD2 + pMW118::yahN | 13.8 | 34.5 |
| W3110(tyrA)/pCABD2 + pMW118::yeaS | 12.7 | 31.8 |
| W3110(tyrA)/pCABD2 + pMW118::yfiK | 12.2 | 30.5 |

The result in Table 3 shows that the produced amount and the yield based on consumed sugar of lysine is increased by enhancement of YahN and YeaS.

(2). As the lysine-producing bacterium belonging to the genus *Escherichia*, *E. coli* strain VL614 was used. This strain is a derivative of the known *E. coli* strain VL613 (SU Patent No. 1354458). In turn, the strain VL613 was obtained from the known strain Gif102 (Theze, J. and Saint Girons. J. Bacteriol., 118, 990–998, 1974) in the three steps:

At the first step the mutants resistant to 2 mg/ml S-(2-aminoethyl)-L-cysteine were selected and among them the strain VL611 was found capable to produce L-lysine.

At the second step the genes involved in sucrose utilization and located on the transposon Tn2555 (Doroshenko et al., Mol. Biologiya, 22, 645–658, 1988), were introduced into VL611 using phage P1-mediated transduction giving the strain VL612.

At the third step, the mutation rhtA23 from the strain VKPM B-3996, conferring resistance to threonine and homoserine (U.S. Pat. No. 5,175,107) was introduced into VL612 by phage P1 transduction giving the strain VL613.

The *E. coli* strain VL614 was obtained by transduction of the wild-type allele of the rhtA gene from the *E. coli* strain VKPM B-6204 (MG1655 zbi3058::Tn10) to VL613. Transductants were selected on L-medium containing 10 mg/l tetracyclin, and among them the strain VL614 (rhtA$^+$) sensitive to 10 g/l homoserine was found.

The strain VL614 was transformed with the pYGGA plasmid or with the pOK12 vector to obtain strains VL614/pYGGA (VKPM B-7719) and VL614/pOK12 (VKPM B-7722).

These strains were each cultivated at 37° C. for 18 hours in a nutrient broth with 50 mg/l kanamycin, and 0.3 ml of the obtained culture was inoculated into 3 ml of a fermentation medium (Example 3) containing 0.3 g/l threonine, 0.3 g/l methionine and 50 mg/l kanamycin, in a 20×200 mm test tube, and cultivated at 37° C. for 48 hours with a rotary shaker. After the cultivation, each accumulated amount of lysine and glutamate in the medium was determined by the known method.

The results are shown in Table 4.

TABLE 4

| Strain | Lysine, g/l | Glutamate, g/l |
|---|---|---|
| VL614/pOK12 | 2.6 | 0.8 |
| VL614/pYGGA | 3.6 | 2.2 |

As shown in Table 4, the strain VL614/pYGGA accumulated lysine in a larger amount than the strain VL614/pOK12 in which the yggA gene was not enhanced. Besides, the strain VL614/pYGGA accumulated more glutamic acid than the strain VL614/pOK12.

EXAMPLE 5

Effect of yeaS, yahN, and yfiK DNA Fragments Amplification on Threonine, Alanine, valine and Isoleucine Production As the threonine-producinq bacterium belonging to the genus *Escherichia*, the *E. coli* strain VL2054 was used. This strain was derived from the known *E. coli* strain VKPM B-3996 (U.S. Pat. No. 5,175,107) as follows.

Initially, a new recipient strain was constructed in several steps:

The plasmidless derivative of the strain VKPM B-3996 was selected after spontaneous elimination of pVIC40 plasmid. The wild-type allele of the rhtA gene from the *E. coli* strain VKPM B-6204 (MG1655 zbi3058: Tn10) was introduced into the thus obtained strain by phage P1 mediated transduction as in the Example 4.

A mutation inactivating kan gene of the Tn5 transposon inserted into the tdh gene was obtained after NG mutagenesis and selection of kanamycin-sensitive cells still unable to degrade threonine. Thus the strain VL2053 was obtained.

On the other hand, the threonine operon from pVIC40 was cloned into integrative Mud vector under the $P_R$ promoter of the phage lambda. In addition, the cat gene of Tn9 conferring the resistance to chloramphenicol was cloned into the same vector. The construct thus obtained was inserted into the chromosome of the *E. coli* strain C600 by use of the known method (U.S. Pat. No. 5,595,889) and transduced from the thus obtained strain to VL2053, giving the new plasmidless threonine-producing strain VL2054. This strain accumulated in culture broth also alanine, valine and isoleucine.

The strain VL2054 was transformed with each of the plasmids pYEAS, pYFIK, and with the vector pUC21 to obtain *E. coli* strains VL2054/pYEAS (VKPM B-7707), VL2054/pYFIK (VKPM B-7712) and VL2054/pUC21 (VKPM B-7708).

These strains were each cultivated at 37° C. for 18 hours in a nutrient broth with 100 mg/l ampicillin, and 0.3 ml of the obtained culture was inoculated into 3 ml of a fermentation medium (Example 3) containing 100 mg/l ampicillin, in a 20×200 mm test tube, and cultivated at 37° C. for 48 hours with a rotary shaker. After the cultivation, each accumulated amount of threonine, alanine, valine and isoleucine in the medium was determined by known method.

The results are shown in Table 5.

As shown in Table 5, the strain VL2054/pYFIK accumulated threonine in a larger amount than the strain VL2054/pUC21 in which the yfiK gene was not enhanced. Besides, the strain VL2054/pYEAS accumulated more alanine, valine and isoleucine than the strain VL2054/pUC21 in which the yeaS gene was not enhanced.

TABLE 5

| | Amino acid accumulation, g/l | | | |
|---|---|---|---|---|
| Strain | Threonine | Alanine | Valine | Isoleucine |
| VL2054/pUC21 | 5.8 | 0.4 | 0.31 | 0.15 |
| VL2054/pYEAS | 5.2 | 1.4 | 0.52 | 0.45 |
| VL2054/pYFIK | 8.8 | 0.5 | 0.22 | 0.14 |

EXAMPLE 6

Effect of yeaS and yfiK DNA Fragments Amplification on Histidine Production

As the histidine-producing bacterium belonging to the genus *Escherichia*, the strain *E. coli* VL2160 was used. This strain was obtained on the basis of the known strain NK5526 hisG::Tn10 (VKPM,B-3384) by phage P1-mediated transduction of the hisG$^R$ mutation desensitizing ATP-phosphoribosyltransferase from the strain CC46 (Astvatsaturianz et al., Genetika, 24, 1928–1934, 1988). The strain *E. coli* VL2160 was transformed with each of the plasmids pYEAS, pYFIK, and with the vectors pUC21 to obtain *E. coli* strains VL2160/pYEAS (VKPM B-7753), *E. coli* VL2160/pYFIK (VKPM B-7754), *E. coli* VL2160/pUC21 (VKPM B-7752).

These strains were each cultivated at 37° C. for 18 hours in a nutrient broth with 100 mg/l ampicillin, and 0.3 ml of the obtained culture was inoculated into 3 ml of the fermentation medium (Example 3) containing an increased amount of yeast extract (3 g/l) and 100 mg/l ampicillin, in a 20×200 mm test tube, and cultivated at 34° C. for 68 hours with a rotary shaker.

After the cultivation, an accumulated amount of histidine in the medium was determined by known method. The results are shown in Table 6.

TABLE 6

| Strain | Histidine, g/l |
|---|---|
| VL2160/pUC21 | 1.2 |
| VL2160/pYEAS | 1.8 |
| VL2160/pYFIK | 1.4 |

As shown in Table 6, the strains *E. coli* VL2160/pYEAS and *E. coli* VL2160/pYFIK accumulated histidine in a larger amount than the strain *E. coli* VL2160/pUC21 in which the yeaS and yfiK genes were not enhanced.

EXAMPLE 7

Effect of yahN, yfiK and yeaS DNA Fragments Amplification on Proline Production

As the proline-producing bacterium belonging to the genus *Escherichia*, the strain VL2151 (W3350 proB* ΔputAP Tn10) was used. This strain was obtained by transduction into W3350 of ΔputAP mutation linked to Tn10 and selecting tetracycline-resistant transductants unable to utilize proline as a sole carbon source. The thus obtained strain W3350 ΔputAP Tn10 was mutagenized with NG and mutants resistant to 20 mg/l of 3,4-dehydro-DL-proline were selected. Among them the strain VL2151 (W3350 proB* ΔputAP Tn10) was found capable to produce proline.

The strain *E. coli* VL2151 was transformed with each of the plasmids pYEAS, pYFIK, pYAHN and with the vectors pUC21 to obtain *E. coli* strains VL2151/pYEAS (VKPM B-7714), VL2151/pYFIK (VKPM B-7713), VL2151/pYAHN (VKPM B-7748) and *E. coli* VL2151/pUC21 (VKPM B-7715).

These strains were each cultivated at 37° C. for 18 hours in a nutrient broth with 100 mg/l ampicillin, and 0.3 ml of the obtained culture was inoculated into 3 ml of a fermentation medium (Example 3) containing 100 mg/l ampicillin, in a 20×200 mm test tube, and cultivated at 37° C. for 48 hours with a rotary shaker. After the cultivation, an accumulated amount of proline in the medium was determined by known method. The results are shown in Table 7.

TABLE 7

| Strain | Proline, g/l |
| --- | --- |
| VL2151/pUC21 | 1.8 |
| VL2151/pYAHN | 2.2 |
| VL2151/pYEAS | 2.1 |
| VL2151/pYFIK | 2.5 |

As shown in Table 7, the strains *E. coli* VL2151/pYFIK, *E. coli* VL2151/pYAHN and *E. coli* VL2151/pYEAS accumulated praline in a larger amount than the strain *E. coli* VL2151/pUC21 in which the yfiK, yahN and yeaS genes were not enhanced. The amplification of yfiK gene had the most pronounced effect.

EXAMPLE 8

Effect of yggA DNA Fragments Amplification on Arginine Production

As arginine-producing bacterium belonging to the genus *Escherichia*, the strain W3350 argE::Tn10/pKA10 was used. This strain harbors a plasmid, pKA10, containing DNA region from *Corynebacterium* (*Brevibacterium*) *flavum* which complements at least argA and argE mutations in the recipient strain of *E. coli* K-12 (Kharitonov A. and Tarasov A. P. Molecular Genetics, Microbiology and Virology. No. 9, 29–33, 1986).

The strain *E. coli* W3350 argE::Tn10/pKA10 was transformed with the plasmid pYGGA, or with the vector pOK12 to obtain the strains *E. coli* W3350 argE::Tn10/pKA10, pYGGA (VKPM B-7716) and *E. coli* W3350 argE::Tn10/pKA10, pOK12 (VKPM B-7718).

The thus obtained transformants were each cultivated at 37° C. for 18 hours in a nutrient broth with 100 mg/l ampicillin and 50 mg/l kanamycin, and 0.3 ml of the obtained culture was inoculated into 3 ml of a fermentation medium (Example 3) containing 100 mg/l ampicillin and 50 mg/l kanamycin, in a 20×200 mm test tube, and cultivated at 37° C. for 48 hours with a rotary shaker. After the cultivation, an accumulated amount of arginine in the medium was determined by known method.

The results are shown in Table 8.

TABLE 8

| Strain | Arginine, g/l |
| --- | --- |
| W3350 argE::Tn10/pKA10, pOK12 | 0.11 |
| W3350 argE::Tn10/pKA10, pYGGA | 0.46 |

As shown in Table 8, the strains *E. coli* W3350 argE::Tn10/pKA10, pYGGA accumulated arginine in a larger amount than the strain *E. coli* W3350 argE::Tn10/pKA10, pUC21 in which the yggA gene was not enhanced.

The following *E. coli* strains have been deposited (according to international deposition based on Budapest Treaty) in the Russian National Collection of Industrial Microorganisms (VKPM) on Dec. 29, 1998 under the accession numbers shown in parenthesis.

AJ13199/pUC21 (VKPM B-7728)
AJ13199/pYAHN (VKPM B-7729)
AJ13199/pYEAS (VKPM B-7731)
AJ13199/pYFIK (VKPM B-7730)
VL614/pYGGA (VKPM B-7719)
VL614/pOK12 (VKPM B-7722)
VL2054/pYEAS (VKPM B-7707)
VL2054/pYFIK (VKPM B-7712)
VL2054/pUC21 (VKPM B-7708)
VL2160/pYEAS (VKPM B-7753)
VL2160/pYFIK (VKPM B-7754) VL2160/pUC21 (VKPM B-7752)
VL2151/pYFIK (VKPM B-7713)
VL2151/pYEAS (VKPM B-7714)
VL2151/pYAHN (VKPM B-7748)
VL2151/pUC21 (VKPM B-7715)
W3350 argE::Tn10/pKA10, pYGGA (VKPM B-7716)
W3350 argE::Tn10/pKA10, pOK12 (VKPM B-7718)

What is claimed is:

1. A method for producing an L-amino acid selected from the group consisting of L-glutamic acid and L-proline, comprising:

cultivating a bacterium in a culture medium, to produce and accumulate the L-amino acid in the medium, and recovering the L-amino acid from the medium, said bacterium belonging to the genus *Escherichia* and having the ability to produce an L-amino acid selected from the group consisting of L-proline and L-glutamic acid, wherein an expression amount of a protein having an amino acid sequence shown in SEQ ID NO: 10 is increased relative to the expression of said protein in a wild-type strain MG1655 or W3110 by increasing the copy number of a DNA coding for said protein in said bacterium or by replacing the native promoter with a stronger promoter for expression of a DNA coding for said protein.

2. The method of claim 1, wherein the copy number of a DNA coding for said protein in a bacterium is increased.

3. The method of claim 2, wherein said DNA is carried on a multicopy vector in the bacterium.

4. The method of claim 2, wherein said DNA is carried on a transposon in the bacterium.

5. The method of claim 1, wherein the L-amino acid is L-glutamic acid.

6. The method of claim 1, wherein the L-amino acid is L-proline.

* * * * *

SEQUENCE LISTING

<160> NUMBER OF SEQ ID NOS: 24

<210> SEQ ID NO 1
<211> LENGTH: 27

-continued

```
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 1
ggcgagctcc cagtaaccgg aaataag                                           27

<210> SEQ ID NO 2
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 2
cgctctagaa aggaccacgc attacgg                                           27

<210> SEQ ID NO 3
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 3
ggcgagctca gattggttag catattc                                           27

<210> SEQ ID NO 4
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
cggtctagaa tcagcgaaga atcaggg                                           27

<210> SEQ ID NO 5
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 5
ggcgagctca tgttccgtgt cgggtac                                           27

<210> SEQ ID NO 6
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 6
```

<210> SEQ ID NO 7
<211> LENGTH: 35
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 7
ctctgaattc tctcttatta gtttttctga ttgcc                              35

<210> SEQ ID NO 8
<211> LENGTH: 38
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 8
cgtgacctgc agcgttctca cagcgcggta gcctttaa                           38

<210> SEQ ID NO 9
<211> LENGTH: 672
<212> TYPE: DNA
<213> ORGANISM: Escherichia coli
<220> FEATURE:
<221> NAME/KEY: CDS
<222> LOCATION: (1)..(672)

<400> SEQUENCE: 9

```
atg atg cag tta gtt cac tta ttt atg gat gaa atc act atg gat cct     48
Met Met Gln Leu Val His Leu Phe Met Asp Glu Ile Thr Met Asp Pro
1               5                   10                  15 ttg cat gcc gtt tac ctg acc gta gga ctg ttc gtg att act ttt ttt     96
Leu His Ala Val Tyr Leu Thr Val Gly Leu Phe Val Ile Thr Phe Phe
                20                  25                  30 aat ccg gga gcc aat ctc ttt gtg gta gta caa acc agc ctg gct tcc    144
Asn Pro Gly Ala Asn Leu Phe Val Val Val Gln Thr Ser Leu Ala Ser
            35                  40                  45 ggt cga cgc gca ggg gtg ctg acc ggg ctg ggc gtg gcg ctg ggc gat    192
Gly Arg Arg Ala Gly Val Leu Thr Gly Leu Gly Val Ala Leu Gly Asp
50                  55                  60 gca ttt tat tcc ggg ttg ggt ttg ttt ggt ctt gca acg cta att acg    240
Ala Phe Tyr Ser Gly Leu Gly Leu Phe Gly Leu Ala Thr Leu Ile Thr
65                  70                  75                  80 cag tgt gag gag att ttt tcg ctt atc aga atc gtc ggc ggc gct tat    288
Gln Cys Glu Glu Ile Phe Ser Leu Ile Arg Ile Val Gly Gly Ala Tyr
                85                  90                  95 ctc tta tgg ttt gcg tgg tgc agc atg cgc cgc cag tca aca ccg caa    336
Leu Leu Trp Phe Ala Trp Cys Ser Met Arg Arg Gln Ser Thr Pro Gln
                100                 105                 110 atg agc aca cta caa caa ccg att agc gcc ccc tgg tat gtc ttt ttt    384
Met Ser Thr Leu Gln Gln Pro Ile Ser Ala Pro Trp Tyr Val Phe Phe
            115                 120                 125 cgc cgc gga tta att acc gat ctc tct aac ccg caa acc gtt tta ttt    432
Arg Arg Gly Leu Ile Thr Asp Leu Ser Asn Pro Gln Thr Val Leu Phe
130                 135                 140 ttt atc agt att ttc tca gta aca tta aat gcc gaa aca cca aca tgg    480
Phe Ile Ser Ile Phe Ser Val Thr Leu Asn Ala Glu Thr Pro Thr Trp
```

```
                         145                 150                 155                 160
gca cgt tta atg gcc tgg gcg ggg att gtg ctc gca tca att atc tgg       528
Ala Arg Leu Met Ala Trp Ala Gly Ile Val Leu Ala Ser Ile Ile Trp
                165                 170                 175 cga gtt ttt ctt agt cag gcg ttt tct ttg ccc gct gtg cgt cgt gct       576
Arg Val Phe Leu Ser Gln Ala Phe Ser Leu Pro Ala Val Arg Arg Ala
            180                 185                 190 tat ggg cgt atg caa cgc gtt gcc agt cgg gtt att ggt gca att att       624
Tyr Gly Arg Met Gln Arg Val Ala Ser Arg Val Ile Gly Ala Ile Ile
        195                 200                 205 ggt gta ttc gcg cta cgc ctg att tac gaa ggg gtg acg cag cgg tga       672
Gly Val Phe Ala Leu Arg Leu Ile Tyr Glu Gly Val Thr Gln Arg
    210                 215                 220
```

<210> SEQ ID NO 10
<211> LENGTH: 223
<212> TYPE: PRT
<213> ORGANISM: Escherichia coli

<400> SEQUENCE: 10

```
Met Met Gln Leu Val His Leu Phe Met Asp Glu Ile Thr Met Asp Pro
1               5                   10                  15

Leu His Ala Val Tyr Leu Thr Val Gly Leu Phe Val Ile Thr Phe Phe
                20                  25                  30

Asn Pro Gly Ala Asn Leu Phe Val Val Gln Thr Ser Leu Ala Ser
            35                  40                  45

Gly Arg Arg Ala Gly Val Leu Thr Gly Leu Gly Val Ala Leu Gly Asp
        50                  55                  60

Ala Phe Tyr Ser Gly Leu Gly Leu Phe Gly Leu Ala Thr Leu Ile Thr
65                  70                  75                  80

Gln Cys Glu Glu Ile Phe Ser Leu Ile Arg Ile Val Gly Gly Ala Tyr
                85                  90                  95

Leu Leu Trp Phe Ala Trp Cys Ser Met Arg Arg Gln Ser Thr Pro Gln
                100                 105                 110

Met Ser Thr Leu Gln Gln Pro Ile Ser Ala Pro Trp Tyr Val Phe Phe
            115                 120                 125

Arg Arg Gly Leu Ile Thr Asp Leu Ser Asn Pro Gln Thr Val Leu Phe
        130                 135                 140

Phe Ile Ser Ile Phe Ser Val Thr Leu Asn Ala Glu Thr Pro Thr Trp
145                 150                 155                 160

Ala Arg Leu Met Ala Trp Ala Gly Ile Val Leu Ala Ser Ile Ile Trp
                165                 170                 175

Arg Val Phe Leu Ser Gln Ala Phe Ser Leu Pro Ala Val Arg Arg Ala
            180                 185                 190

Tyr Gly Arg Met Gln Arg Val Ala Ser Arg Val Ile Gly Ala Ile Ile
        195                 200                 205

Gly Val Phe Ala Leu Arg Leu Ile Tyr Glu Gly Val Thr Gln Arg
    210                 215                 220
```

<210> SEQ ID NO 11
<211> LENGTH: 639
<212> TYPE: DNA
<213> ORGANISM: Escherichia coli
<220> FEATURE:
<221> NAME/KEY: CDS
<222> LOCATION: (1)..(639)

<400> SEQUENCE: 11

```
                                                                            -continued gtg ttc gct gaa tac ggg gtt ctg aat tac tgg acc tat ctg gtt ggg              48
Val Phe Ala Glu Tyr Gly Val Leu Asn Tyr Trp Thr Tyr Leu Val Gly
1               5                   10                  15 gcc att ttt att gtg ttg gtg cca ggg cca aat acc ctg ttt gta ctc              96
Ala Ile Phe Ile Val Leu Val Pro Gly Pro Asn Thr Leu Phe Val Leu
                20                  25                  30 aaa aat agc gtc agt agc ggt atg aaa ggc ggt tat ctt gcg gcc tgc             144
Lys Asn Ser Val Ser Ser Gly Met Lys Gly Gly Tyr Leu Ala Ala Cys
            35                  40                  45 ggt gta ttt att ggc gat gcg gta ttg atg ttt ctg gca tgg gct gga             192
Gly Val Phe Ile Gly Asp Ala Val Leu Met Phe Leu Ala Trp Ala Gly
        50                  55                  60 gtg gcg aca tta att aag acc acc ccg ata tta ttc aac att gta cgt             240
Val Ala Thr Leu Ile Lys Thr Thr Pro Ile Leu Phe Asn Ile Val Arg
65                  70                  75                  80 tat ctt ggt gcg ttt tat ttg ctc tat ctg ggg agt aaa att ctt tac             288
Tyr Leu Gly Ala Phe Tyr Leu Leu Tyr Leu Gly Ser Lys Ile Leu Tyr
                85                  90                  95 gcg acc ctg aag ggt aaa aat agc gag gcc aaa tcc gat gag ccc caa             336
Ala Thr Leu Lys Gly Lys Asn Ser Glu Ala Lys Ser Asp Glu Pro Gln
            100                 105                 110 tac ggt gct att ttt aaa cgc gcg tta att ttg agc ctg act aat ccg             384
Tyr Gly Ala Ile Phe Lys Arg Ala Leu Ile Leu Ser Leu Thr Asn Pro
        115                 120                 125 aaa gcc att ttg ttc tat gtg tcg ttt ttc gta cag ttt atc gat gtt             432
Lys Ala Ile Leu Phe Tyr Val Ser Phe Phe Val Gln Phe Ile Asp Val
    130                 135                 140 aat gcc cca cat acg gga att tca ttc ttt att ctg gcg gcg acg ctg             480
Asn Ala Pro His Thr Gly Ile Ser Phe Phe Ile Leu Ala Ala Thr Leu
145                 150                 155                 160 gaa ctg gtg agt ttc tgc tat ttg agc ttc ctg att ata tct ggt gct             528
Glu Leu Val Ser Phe Cys Tyr Leu Ser Phe Leu Ile Ile Ser Gly Ala
                165                 170                 175 ttt gtc acg cag tac ata cgt acc aaa aag aaa ctg gct aaa gtt ggc             576
Phe Val Thr Gln Tyr Ile Arg Thr Lys Lys Lys Leu Ala Lys Val Gly
            180                 185                 190 aac tca ctg att ggt ttg atg ttc gtg ggt ttc gct gcc cga ctg gcg             624
Asn Ser Leu Ile Gly Leu Met Phe Val Gly Phe Ala Ala Arg Leu Ala
        195                 200                 205 acg ctg caa tcc tga                                                         639
Thr Leu Gln Ser
    210

<210> SEQ ID NO 12
<211> LENGTH: 212
<212> TYPE: PRT
<213> ORGANISM: Escherichia coli

<400> SEQUENCE: 12

Val Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
                20                  25                  30

Lys Asn Ser Val Ser Ser Gly Met Lys Gly Gly Tyr Leu Ala Ala Cys
            35                  40                  45

Gly Val Phe Ile Gly Asp Ala Val Leu Met Phe Leu Ala Trp Ala Gly
        50                  55                  60

Val Ala Thr Leu Ile Lys Thr Thr Pro Ile Leu Phe Asn Ile Val Arg
65                  70                  75                  80
```

```
Tyr Leu Gly Ala Phe Tyr Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
            115                 120                 125

Lys Ala Ile Leu Phe Tyr Val Ser Phe Val Gln Phe Ile Asp Val
130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
            195                 200                 205

Thr Leu Gln Ser
    210

<210> SEQ ID NO 13
<211> LENGTH: 588
<212> TYPE: DNA
<213> ORGANISM: Escherichia coli
<220> FEATURE:
<221> NAME/KEY: CDS
<222> LOCATION: (1)..(588)

<400> SEQUENCE: 13 gtg aca ccg acc ctt tta agt gct ttt tgg act tac acc ctg att acc       48
Val Thr Pro Thr Leu Leu Ser Ala Phe Trp Thr Tyr Thr Leu Ile Thr
1               5                   10                  15 gct atg acg cca gga ccg aac aat att ctc gcc ctt agc tct gct acg       96
Ala Met Thr Pro Gly Pro Asn Asn Ile Leu Ala Leu Ser Ser Ala Thr
            20                  25                  30 tcg cat gga ttt cgt caa agt acc cgc gtg ctg gca ggg atg agt ctg      144
Ser His Gly Phe Arg Gln Ser Thr Arg Val Leu Ala Gly Met Ser Leu
        35                  40                  45 gga ttt ttg att gtg atg tta ctg tgt gcg ggc att tca ttt tca ctg      192
Gly Phe Leu Ile Val Met Leu Leu Cys Ala Gly Ile Ser Phe Ser Leu
    50                  55                  60 gca gtg att gac ccg gca gcg gta cac ctt ttg agt tgg gcg ggg gcg      240
Ala Val Ile Asp Pro Ala Ala Val His Leu Leu Ser Trp Ala Gly Ala
65                  70                  75                  80 gca tat att gtc tgg ctg gcg tgg aaa atc gcc acc agc cca aca aag      288
Ala Tyr Ile Val Trp Leu Ala Trp Lys Ile Ala Thr Ser Pro Thr Lys
                85                  90                  95 gaa gac gga ctt cag gca aaa cca atc agc ttt tgg gcc agc ttt gct      336
Glu Asp Gly Leu Gln Ala Lys Pro Ile Ser Phe Trp Ala Ser Phe Ala
            100                 105                 110 ttg cag ttt gtg aac gtc aaa atc att ttg tac ggt gtt acg gca ctg      384
Leu Gln Phe Val Asn Val Lys Ile Ile Leu Tyr Gly Val Thr Ala Leu
            115                 120                 125 tcg acg ttt gtt ctg ccg caa aca cag gcg tta agc tgg gta gtt ggc      432
Ser Thr Phe Val Leu Pro Gln Thr Gln Ala Leu Ser Trp Val Val Gly
        130                 135                 140 gtc agc gtt ttg ctg gcg atg att ggg acg ttt ggc aat gtg tgc tgg      480
Val Ser Val Leu Leu Ala Met Ile Gly Thr Phe Gly Asn Val Cys Trp
145                 150                 155                 160 gcg ctg gcg ggg cat ctg ttt cag cga ttg ttt cgc cag tat ggt cgc      528
```

```
Ala Leu Ala Gly His Leu Phe Gln Arg Leu Phe Arg Gln Tyr Gly Arg
            165                 170                 175 cag tta aat atc gtg ctt gcc ctg ttg ctg gtc tat tgc gcg gta cgc      576
Gln Leu Asn Ile Val Leu Ala Leu Leu Leu Val Tyr Cys Ala Val Arg
            180                 185                 190 att ttc tat taa                                                      588
Ile Phe Tyr
        195

<210> SEQ ID NO 14
<211> LENGTH: 195
<212> TYPE: PRT
<213> ORGANISM: Escherichia coli

<400> SEQUENCE: 14

Val Thr Pro Thr Leu Leu Ser Ala Phe Trp Thr Tyr Thr Leu Ile Thr
1               5                   10                  15

Ala Met Thr Pro Gly Pro Asn Asn Ile Leu Ala Leu Ser Ser Ala Thr
            20                  25                  30

Ser His Gly Phe Arg Gln Ser Thr Arg Val Leu Ala Gly Met Ser Leu
        35                  40                  45

Gly Phe Leu Ile Val Met Leu Leu Cys Ala Gly Ile Ser Phe Ser Leu
    50                  55                  60

Ala Val Ile Asp Pro Ala Ala Val His Leu Leu Ser Trp Ala Gly Ala
65                  70                  75                  80

Ala Tyr Ile Val Trp Leu Ala Trp Lys Ile Ala Thr Ser Pro Thr Lys
                85                  90                  95

Glu Asp Gly Leu Gln Ala Lys Pro Ile Ser Phe Trp Ala Ser Phe Ala
            100                 105                 110

Leu Gln Phe Val Asn Val Lys Ile Ile Leu Tyr Gly Val Thr Ala Leu
        115                 120                 125

Ser Thr Phe Val Leu Pro Gln Thr Gln Ala Leu Ser Trp Val Val Gly
    130                 135                 140

Val Ser Val Leu Leu Ala Met Ile Gly Thr Phe Gly Asn Val Cys Trp
145                 150                 155                 160

Ala Leu Ala Gly His Leu Phe Gln Arg Leu Phe Arg Gln Tyr Gly Arg
                165                 170                 175

Gln Leu Asn Ile Val Leu Ala Leu Leu Leu Val Tyr Cys Ala Val Arg
            180                 185                 190

Ile Phe Tyr
        195

<210> SEQ ID NO 15
<211> LENGTH: 636
<212> TYPE: DNA
<213> ORGANISM: Escherichia coli
<220> FEATURE:
<221> NAME/KEY: CDS
<222> LOCATION: (1)..(636)

<400> SEQUENCE: 15 gtg ttt tct tat tac ttt caa ggt ctt gca ctt ggg gcg gct atg atc       48
Val Phe Ser Tyr Tyr Phe Gln Gly Leu Ala Leu Gly Ala Ala Met Ile
1               5                   10                  15 cta ccg ctc ggt cca caa aat gct ttt gtg atg aat cag ggc ata cgt       96
Leu Pro Leu Gly Pro Gln Asn Ala Phe Val Met Asn Gln Gly Ile Arg
            20                  25                  30 cgt cag tac cac att atg att gcc tta ctt tgt gct atc agc gat ttg      144
Arg Gln Tyr His Ile Met Ile Ala Leu Leu Cys Ala Ile Ser Asp Leu
```

-continued

```
            35                  40                  45
gtc ctg att tgc gcc ggg att ttt ggt ggc agc gcg tta ttg atg cag      192
Val Leu Ile Cys Ala Gly Ile Phe Gly Gly Ser Ala Leu Leu Met Gln
     50                  55                  60 tcg ccg tgg ttg ctg gcg ctg gtc acc tgg ggc ggc gta gcc ttc ttg      240
Ser Pro Trp Leu Leu Ala Leu Val Thr Trp Gly Gly Val Ala Phe Leu
 65                  70                  75                  80 ctg tgg tat ggt ttt ggc gct ttt aaa aca gca atg agc agt aat att      288
Leu Trp Tyr Gly Phe Gly Ala Phe Lys Thr Ala Met Ser Ser Asn Ile
                 85                  90                  95 gag tta gcc agc gcc gaa gtc atg aag caa ggc aga tgg aaa att atc      336
Glu Leu Ala Ser Ala Glu Val Met Lys Gln Gly Arg Trp Lys Ile Ile
            100                 105                 110 gcc acc atg ttg gca gtg acc tgg ctg aat ccg cat gtt tac ctg gat      384
Ala Thr Met Leu Ala Val Thr Trp Leu Asn Pro His Val Tyr Leu Asp
        115                 120                 125 act ttt gtt gta ctg ggc agc ctt ggc ggg caa ctt gat gtg gaa cca      432
Thr Phe Val Val Leu Gly Ser Leu Gly Gly Gln Leu Asp Val Glu Pro
    130                 135                 140 aaa cgc tgg ttt gca ctc ggg aca att agc gcc tct ttc ctg tgg ttc      480
Lys Arg Trp Phe Ala Leu Gly Thr Ile Ser Ala Ser Phe Leu Trp Phe
145                 150                 155                 160 ttt ggt ctg gct ctt ctc gca gcc tgg ctg gca ccg cgt ctg cgc acg      528
Phe Gly Leu Ala Leu Leu Ala Ala Trp Leu Ala Pro Arg Leu Arg Thr
                165                 170                 175 gca aaa gca cag cgc att atc aat ctg gtt gtg gga tgt gtt atg tgg      576
Ala Lys Ala Gln Arg Ile Ile Asn Leu Val Val Gly Cys Val Met Trp
            180                 185                 190 ttt att gcc ttg cag ctg gcg aga gac ggt att gct cat gca caa gcc      624
Phe Ile Ala Leu Gln Leu Ala Arg Asp Gly Ile Ala His Ala Gln Ala
        195                 200                 205 ttg ttc agt tag                                                      636
Leu Phe Ser
    210

<210> SEQ ID NO 16
<211> LENGTH: 211
<212> TYPE: PRT
<213> ORGANISM: Escherichia coli

<400> SEQUENCE: 16

Val Phe Ser Tyr Tyr Phe Gln Gly Leu Ala Leu Gly Ala Ala Met Ile
 1               5                  10                  15

Leu Pro Leu Gly Pro Gln Asn Ala Phe Val Met Asn Gln Gly Ile Arg
                20                  25                  30

Arg Gln Tyr His Ile Met Ile Ala Leu Leu Cys Ala Ile Ser Asp Leu
            35                  40                  45

Val Leu Ile Cys Ala Gly Ile Phe Gly Gly Ser Ala Leu Leu Met Gln
        50                  55                  60

Ser Pro Trp Leu Leu Ala Leu Val Thr Trp Gly Gly Val Ala Phe Leu
 65                  70                  75                  80

Leu Trp Tyr Gly Phe Gly Ala Phe Lys Thr Ala Met Ser Ser Asn Ile
                 85                  90                  95

Glu Leu Ala Ser Ala Glu Val Met Lys Gln Gly Arg Trp Lys Ile Ile
            100                 105                 110

Ala Thr Met Leu Ala Val Thr Trp Leu Asn Pro His Val Tyr Leu Asp
        115                 120                 125

Thr Phe Val Val Leu Gly Ser Leu Gly Gly Gln Leu Asp Val Glu Pro
```

```
            130                 135                 140
Lys Arg Trp Phe Ala Leu Gly Thr Ile Ser Ala Ser Phe Leu Trp Phe
145                 150                 155                 160

Phe Gly Leu Ala Leu Leu Ala Ala Trp Leu Ala Pro Arg Leu Arg Thr
                165                 170                 175

Ala Lys Ala Gln Arg Ile Ile Asn Leu Val Val Gly Cys Val Met Trp
            180                 185                 190

Phe Ile Ala Leu Gln Leu Ala Arg Asp Gly Ile Ala His Ala Gln Ala
                195                 200                 205

Leu Phe Ser
    210

<210> SEQ ID NO 17
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 17
gtgtggaacc gacgccggat                                              20

<210> SEQ ID NO 18
<211> LENGTH: 23
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 18
tgttgtatgg tacggggttc gag                                          23

<210> SEQ ID NO 19
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 19
ctttgccaat cccgtctccc                                              20

<210> SEQ ID NO 20
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 20
gccccatgca taacggaaag                                              20

<210> SEQ ID NO 21
<211> LENGTH: 26
<212> TYPE: DNA
<213> ORGANISM: Artificial Sequence
<220> FEATURE:
```

```
<221> NAME/KEY: misc_feature
<223> OTHER INFORMATION: Description of Artificial Sequence: synthetic
      DNA

<400> SEQUENCE: 21
gaagatcttg taggccggat aaggcg                                              26

<210> SEQ ID NO 22
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 22
tggttttacc aattggccgc                                                    20

<210> SEQ ID NO 23
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 23
acttctcccg cgagccagtt c                                                  21

<210> SEQ ID NO 24
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 24
ggcaagctta gcgcctctgt t                                                  21
```